United States Patent [19]

Wada et al.

[11] Patent Number: 6,127,454

[45] Date of Patent: *Oct. 3, 2000

[54] WATER-ABSORBING AGENT AND PRODUCTION PROCESS THEREFOR

[75] Inventors: Katsuyuki Wada; Kinya Nagasuna, both of Himeji, Japan

[73] Assignee: Nippon Shokubai Co., Ltd., Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/947,094

[22] Filed: Oct. 8, 1997

[30] Foreign Application Priority Data

Oct. 15, 1996 [JP] Japan .................................... 8-271950
Jan. 24, 1997 [JP] Japan .................................... 9-011762

[51] Int. Cl.[7] .............................. C08F 8/00; A61L 15/00

[52] U.S. Cl. .......................... 523/200; 523/202; 523/205; 523/206; 525/242

[58] Field of Search .................................. 523/200, 202, 523/205, 206; 525/242

[56] References Cited

U.S. PATENT DOCUMENTS

| | | |
|---|---|---|
| 4,734,478 | 3/1988 | Tsubakimoto et al. . |
| 4,794,166 | 12/1988 | Engelhardt et al. . |
| 5,002,986 | 3/1991 | Fujiura et al. . |
| 5,032,628 | 7/1991 | Choi et al. . |
| 5,147,343 | 9/1992 | Kellenberger . |
| 5,149,335 | 9/1992 | Kellenberger et al. . |
| 5,328,935 | 7/1994 | Van Phan et al. . |
| 5,422,405 | 6/1995 | Dairoku et al. . |
| 5,597,873 | 1/1997 | Chambers et al. ................... 525/330.1 |
| 5,610,208 | 3/1997 | Dairoku et al. . |
| 5,672,633 | 9/1997 | Brehm et al. . |
| 5,760,080 | 6/1998 | Wada et al. . |
| 5,797,893 | 8/1998 | Wada et al. . |

FOREIGN PATENT DOCUMENTS

| | | |
|---|---|---|
| 0 530 438 A1 | 3/1993 | European Pat. Off. . |
| 0 574 202 A1 | 12/1993 | European Pat. Off. . |
| 43 33 056 A1 | 3/1995 | Germany . |
| 63-99861 | 5/1988 | Japan . |
| 2-34167 | 2/1990 | Japan . |
| WO 93/05080 | 3/1993 | WIPO . |
| WO 94/09043 | 4/1994 | WIPO . |
| WO 94/20547 | 9/1994 | WIPO . |
| WO 96/05234 | 2/1996 | WIPO . |

*Primary Examiner*—Nathan M. Nutter

[57] ABSTRACT

The invention provides a water-absorbing agent, which has high absorption capacity and excellent absorption efficiency under increased pressure and can display excellent water absorption properties when used for sanitary materials even if the resin concentration of a water-absorbent resin is high. The water-absorbing agent has an absorption capacity of 30 (g/g) or more and the below-defined absorption efficiency of 0.7 or more under increased pressure. This agent can be obtained by heating in the presence of a surface-crosslinking agent a water-absorbent resin having an absorption capacity of 40 (g/g) or more and an amount of an eluting component of 1 wt % or less relative to the water-absorbent resin, or by: polymerizing a water-absorbent resin in the presence of a chain transfer agent; treating the polymerized resin with a hydrophilic solution; and heating the treated resin in the presence of a surface-crosslinking agent.

$$\text{absorption efficiency under increased pressure} = \frac{\text{absorption capacity of upper swollen gel layer of water absorbing agent under increased pressure}}{\text{absorption capacity of lower swollen gel layer of water absorbing agent under increased pressure}}$$

16 Claims, 1 Drawing Sheet

WATER-ABSORBING AGENT AND PRODUCTION PROCESS THEREFOR

BACKGROUND OF THE INVENTION

A. Technical Field

The present invention relates to a water-absorbing agent and a production process therefor, and in more detail, relates to: a water-absorbing agent, which 1) displays very high absorption capacity even under an increased pressure, 2) displays only a small difference between swelling capacities at positions in a layer, 3) displays uniform swelling action even when the density of a water-absorbent resin is high and even when a swollen gel of the resin is present in the form of the layer, and 4) is favorably used for sanitary materials such as disposable diapers, sanitary napkins, and incontinence pads; and a production process to provide the water-absorbing agent.

B. Background Art

In recent years, water-absorbent resins have been widely used in the manufacture of sanitary materials, such as disposable diapers, sanitary napkins, and incontinence pads, in order to allow the water-absorbent resins to absorb humors.

Known examples of water-absorbent resins are as follows: crosslinked products of partially neutralized polyacrylic acid; hydrolyzed products of starch-acrylonitrile graft polymers; neutralized products of starch-acrylic acid graft polymers; saponified products of vinyl acetate-acrylic ester copolymers; crosslinked matters of carboxymethylcellulose; hydrolyzed products of acrylonitrile copolymers or of acrylamide copolymers, or crosslinked products of these hydrolyzed products; crosslinked products of cationic monomers; crosslinked isobutylene-maleic acid copolymers; and crosslinked products of 2-acrylamido-2-methylpropanesulfonic acid with acrylic acid.

It is conventionally requested that the above-mentioned water-absorbent resins have the following properties: when contacting aqueous liquids such as humors, they display high absorption capacity, excellent absorption speed, liquid-permeability, gel strength of swollen gel, and a suction force, which draws water from base materials containing aqueous liquids, and so on. However, relationships between these properties do not necessarily display positive correlations. For example, the higher the absorption capacity, the lower some other properties such as liquid-permeability, gel strength, and absorption speed. Thus, for improving the water-absorption properties of a water-absorbent resin for a good balance among the properties, various methods have been proposed so far in this art where the neighborhood of the surface of the water-absorbent resin is crosslinked. For example, methods are known in each of which the following are used as crosslinking agents: polyhydric alcohols; polyglycidyl compounds, polyaziridine compounds, polyamine compounds, or polyisocyanate compounds, glyoxal; polyvalent metals, silane coupling agents; combinations of epoxy compounds with hydroxy compounds; alkylene carbonates.

In addition, methods are also known in which when a crosslinking agent is added, the following are allowed to be present: inert inorganic powders; dihydric alcohols; ether compounds; water-soluble polymers; alkylene oxide adducts of monohydric alcohols, or organic acid salts, or lactams, as an attempt to more uniformly disperse the crosslinking agent onto the surface of a water-absorbent resin and to carry out uniform surface-crosslinking in a crosslinking reaction.

The balance among the properties of a water-absorbent resin may be improved by the above-mentioned methods, but it is still difficult to say that the resultant balance is sufficient. As to the above-mentioned conventional water-absorbent resins as used for absorbent material in sanitary articles, the following are, for example, known: an water-absorbent sanitary article containing a water-absorbent resin of which the amount of the water absorption, especially that under an increased pressure, and the gel fracture strength are specified (Japanese Patent Application Publication (Kokai) No. 63-99861); a disposable diaper containing a water-absorbent resin of which the amount of the water absorption or the water absorption speed under an increased pressure is specified Japanese Patent Application Publication (Kokai) No. 2-34167); an absorbing agent containing a water-absorbent resin of which the amount of the water absorption under an increased pressure and the particle diameter under an increased pressure are specified (European Patent No. 339461); a water-absorbent resin containing a water-absorbent resin of which the water absorption speed or the amount of the water absorption under an increased pressure in a short time is specified (European Patent No. 443627). However, further enhancement of the quality is demanded. Under current circumstances, especially considering necessary properties of water-absorbent resins as used for absorbent material in recently trendy sanitary articles that use a large amount of water-absorbent resin and are thinned, properties resultant from the above-mentioned conventional methods have not yet attained a sufficient level.

That is to say, "an absorption capacity under a high load (e.g. 50 $g/cm^2$) (which may hereinafter be referred to as absorption capacity under an increased pressure) is so excellent that sufficient absorbency can be displayed even if a heavier load is applied during the attachment" This is one of the necessary properties of water-absorbent resins as used for thin type absorbent material containing water-absorbent resins of high concentration. This necessary property can be relatively enhanced by the above-mentioned surface crosslinking methods, but sufficient absorbency can be displayed with regard to the entirety of the absorbent material.

SUMMARY OF THE INVENTION

A. Object of the Invention

An object of the present invention is to provide: a water-absorbing agent which, when used for a thin type absorbent material containing a water-absorbing absorbent resin of high concentration, can display not only high absorption capacity under an increased pressure but also sufficient absorbency of the absorbent material; and a production process for the water-absorbing agent.

B. Disclosure of the Invention

According to the present inventor's findings, even a water-absorbing agent having high absorption capacity under an increased pressure cannot display sufficient absorbency of an absorbent material 1) when there is a great difference between swelling capacities at upper and lower positions, in a swollen gel layer of a water-absorbent resin which is present in high concentration and in high density and 2) when the resin cannot swell so uniformly that inherent absorbency of the resin can be displayed.

Thus, the present inventors further studied to obtain a water-absorbent resin having not only high absorption capacity under an increased pressure but also properties (which may hereinafter be referred to as absorption efficiency under an increased pressure) in which: even when the water-absorbent resin is present in high concentration and in high density there is only a small difference between swelling capacities at upper and lower positions in a swollen gel layer of the resin, and the resin can swell so uniformly that inherent absorbency of the resin can be displayed. As a result, the inventors attained the present invention.

That is to say, in the present invention, the absorption capacity under an increased pressure is high, and the absorption efficiency under an increased pressure is also excellent, and excellent water absorption properties can be displayed even if the resin concentration of a water-absorbent resin is enhanced when the resin is used for sanitary materials, and the water absorbency of the resin can efficiently be displayed even under high concentration.

The present invention provides:

"a water-absorbing agent, having an absorption capacity of 30 (g/g) or more and an absorption efficiency of 0.7 or more under an increased pressure, wherein the absorption efficiency under the increased pressure is shown by the following equation:

$$\text{absorption efficiency under increased pressure} = \frac{\text{absorption capacity of upper swollen gel layer of water absorbing agent under increased pressure}}{\text{absorption capacity of lower swollen gel layer of water absorbing agent under increased pressure}};$$

"a water-absorbing agent, having an absorption capacity of a lower swollen gel layer of 45 (g/g) or more and an absorption efficiency of 0.4 or more under an increased pressure, wherein the absorption efficiency under the increased pressure is shown by the following equation:

$$\text{absorption efficiency under increased pressure} = \frac{\text{absorption capacity of upper swollen gel layer of water absorbing agent under increased pressure}}{\text{absorption capacity of lower swollen gel layer of water absorbing agent under increased pressure}};$$

"a water-absorbing agent, having an absorption capacity of a lower swollen gel layer of 30 (g/g) or more and an absorption efficiency of 0.3 or more under an increased pressure, wherein the absorption efficiency under the increased pressure is shown by the following equation:

$$\text{absorption efficiency under increased pressure} = \frac{\text{absorption capacity of upper swollen gel layer of water absorbing agent under increased pressure}}{\text{absorption capacity of lower swollen gel layer of water absorbing agent under increased pressure}};$$

and wherein the relationship between the absorption efficiency and the absorption capacity of the lower swollen gel layer under the increased pressure is defined by the following equation:

absorption efficiency under increased pressure$>1.82-2.93 \times 10^{-2} \times$ (absorption capacity of lower swollen gel layer under increased pressure);"

"a process for producing a water-absorbing agent, comprising the step of heating in the presence of a surface-crosslinking agent a water-absorbent resin having an absorption capacity of 40 (g/g) or more and an amount of an eluting component of 1 part by weight or less per 100 parts by weight of the water-absorbent resin;"

"a process for producing a water-absorbing agent, comprising the steps of: polymerizing a water-absorbent resin in the presence of a water-soluble chain transfer agent; treating the polymerized water-absorbent resin with a hydrophilic solution; and heating the treated water-absorbent resin in the presence of a surface-crosslinking agent;" and "a process for producing a water-absorbing agent, comprising the steps of: treating with a hydrophilic solution a water-absorbent resin of which the weight-average molecular weight of an eluting component is 200,000 or less; and heating the treated water-absorbent resin in the presence of a surface-crosslinking agent."

These and other objects and the advantages of the present invention will be more fully apparent from the following detailed disclosure.

DETAILED DESCRIPTION OF THE INVENTION

Figure 1:
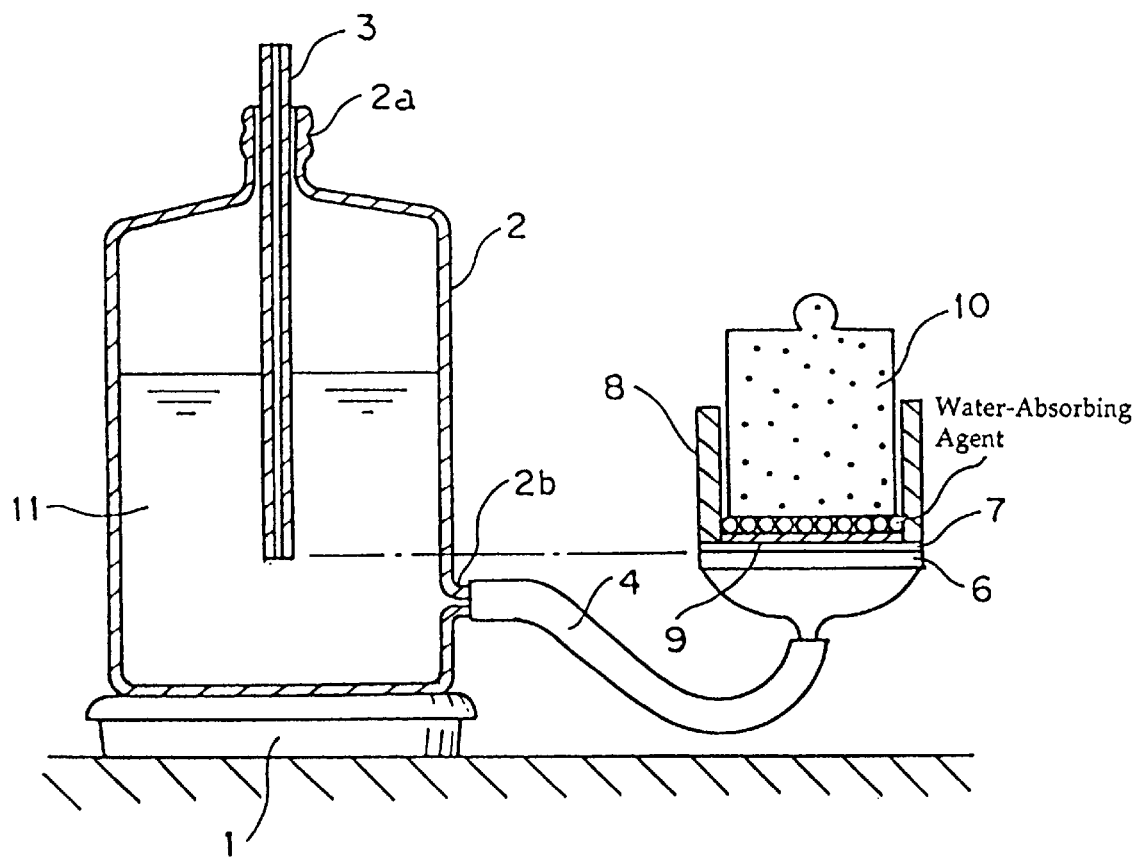
FIG. 1 is a schematic section of a measurement apparatus as used to measure the absorption capacity under an increased pressure which is one of properties that the water-absorbing agent of the present invention displays.

Hereinafter, a detailed description is made of the water-absorbing agent of the present invention along with the production process therefor.

The present invention is a water-absorbent resin, which has an absorption capacity of a specific value or more and where the amount of an eluting component, flowing out of the surface of an unsaturated swollen gel, is reduced to a specific value or less, and which is first obtained. The surface of the resin is then crosslinked.

It is already known that a water-absorbent resin generally contains an eluting component, but an attempt has not yet been made to further subject to a surface-crosslinking treatment a resin of which the amount of the flow of the eluting component out of the surface of an unsaturated swollen gel is reduced to a certain level or lower. The water-absorbent resin as used in the present invention is most characterized in that a water-absorbent resin of which the amount of the flow of the eluting component out of the surface of an unsaturated swollen gel is reduced to a specific level or lower in a specific manner is subjected to a surface-crosslinking treatment.

When a water-absorbent resin is subjected to a surface-crosslinking treatment, the absorption capacity under an increased pressure under a high load can be enhanced to a specific level, for example, 30 (g/g), or higher even if the resin contains a specific amount or more of the eluting component, but it is difficult to obtain a high value of absorption efficiency under an increased pressure. For the first time, however, the present invention process has made it possible to obtain a water-absorbing agent that is excellent both in the absorption capacity under an increased pressure and in the absorption efficiency under an increased pressure.

Hereinafter, the present invention is explained in more detail.

The water-absorbent resin which can be used in the present invention absorbs a large amount of water, a physiological salt solution, and urine and swells with these fluids, and thereby forms a substantially water-insoluble hydrogel, and has an absorption capacity of 40 (g/g) or more with a physiological salt solution, as mentioned below, and a reduced amount of the eluting component of 1 part by weight or less per 100 parts by weight of the water-absorbent resin. In addition, the water-absorbent resin is more preferably such as can be handled as a powder having a water content of 10 % by weight or less, most preferably, 5% by weight or less, of the water-absorbent resin.

A typical example of the water-absorbent resin is a hydrophilic polymer having a crosslinked structure as obtained by polymerizing a hydrophilic monomer comprising a major proportion of acrylic acid or a salt thereof. Examples of such a hydrophilic polymer include: partially neutralized, crosslinked polyacrylic acid polymers; crosslinked and partially neutralized starch-acrylic acid graft polymers; isobutylene-maleic acid copolymers; saponified products of vinyl acetate-acrylic acid copolymers; hydrolyzed products of acrylamide (co)polymers; hydrolyzed products of acrylonitrile polymers. Particularly, polyacrylic salt-crosslinked polymers are preferable. As to the polyacrylic salt-crosslinked polymers, it is preferable that 50–95 mol %, more preferably, 60–90 mol %, of acid groups in the polymers are neutralized. Examples of the salt include alkaline metal salts, ammonium salts, and amine salts. The neutralization may be carried out either to a monomer before polymerization or to a hydrogel polymer during or after polymerization.

The water-absorbent resin as used in the present invention may be such as obtained by (co)polymerizing monomers other than the above-mentioned acrylic acid and salt thereof as preferably used as the major monomer component. Specific examples of the above-mentioned other monomers include: anionic unsaturated monomers, such as methacrylic acid, maleic acid, vinylsulfonic acid, styrenesulfonic acid, 2-(meth) acrylamido-2-methylpropanesulfonic acid, 2-(meth) acryloylethanesulfonic acid, and 2-(meth) acryloylpropanesulfonic acid, and salts thereof; nonionic hydrophilic group-containing unsaturated monomers, such as acrylamide, methacrylamide, N-ethyl(meth)acrylamide, N-n-propyl(meth)acrylamide, N-isopropyl(meth) acrylamide, N,N-dimethyl (meth)acrylamide, 2-hydroxyethyl (meth)acrylate, 2-hydroxypropyl (meth) acrylate, methoxypolyethylene glycol (meth)acrylate, polyethylene glycol mono(meth)acrylate, vinylpyridine, N-vinylpyrrolidone, N-acrylolpiperidine, and N-acryloylpyrrolidine; cationic unsaturated monomers, such as N,N-dimethylaminoethyl (meth)acrylate, N,N-diethylaminoethyl (meth)acrylate, N,N-dimethylaminopropyl (meth)acrylate, and N,N-dimethylaminopropyl(meth)acrylamide, and quaternary salts thereof. The amount of these monomers other than acrylic acid, as used, is usually in the range of from 0 mol % to less than 50 mol %, and preferably in the range of from 0 to 30 mol %, but the amount is not especially limited to these ranges.

Examples of the crosslinked structure of the water-absorbent resin as used in-the present invention include: a self-crosslinked type without any crosslinking agent; and a type as formed by copolymerizing or reacting an internal crosslinking agent having two or more polymerizable unsaturated groups or two or more reactive groups. Although the type as formed by copolymerizing or reacting the internal crosslinking agent is preferable, the crosslinking density needs to be adjusted such that the absorption capacity with a physiological salt solution can be 40 (g/g) or more.

Specific examples of the internal crosslinking agent include N,N'-methylenebis (meth)acrylamide, (poly) ethylene glycol di(meth)acrylate, (poly)propylene glycol di(meth)acrylate, trimethylolpropane tri(meth)acrylate, trimethylolpropane di(meth)acrylate, glycerol tri(meth) acrylate, glycerol acrylate methacrylate, ethylene oxide-modified trimethylolpropane tri(meth)acrylate, pentaerythritol tetra(meth)acrylate, dipentaerythritol hexa (meth)acrylate, triallyl cyanurate, triallyl isocyanurate, triallyl phosphate, triallylamine, poly(meth)allyloxyalkane, (poly)ethylene glycol diglycidyl ether, glycerol diglycidyl ether, ethylene glycol, polyethylene glycol, propylene glycol, glycerol, pentaerythritol, ethylenediamine, polyethyleneimine, glycidyl (meth)acrylate. In addition, these internal crosslinking agents may be used in combinations of two or more thereof. Particularly, considering water absorption properties of the resultant water-absorbent resin, it is preferable to essentially use a compound having two or more polymerizable unsaturated groups as the internal crosslinking agent. The amount of the internal crosslinking agent, as used, is in the range of 0.005 to 3 mol %, more preferably, 0.01 to 1.5 mol %, of the aforementioned monomer component.

In addition, when the polymerization is carried out, hydrophilic high molecules, such as starch-cellulose, derivatives of starch-cellulose, polyvinyl alcohol, polyacrylic acid (salt), and polyacrylic acid (salt)-crosslinked products, or chain transfer agents, such as hypophosphorous acid (salt), may be added.

When the above-mentioned monomer comprising a major proportion of acrylic acid or a salt thereof is polymerized to obtain the water-absorbent resin as used in the present invention, bulk polymerization or precipitation polymerization can be carried out. Considering the performance or the ease of controlling the polymerization, however, it is preferable to carry out aqueous solution polymerization or reversed-phase suspension polymerization using an aqueous solution of the monomer.

In addition, when the polymerization is carried out, the following can be used: radical polymerization initiators such as potassium persulfate, ammonium persulfate, sodium persulfate, t-butyl hydroperoxide, hydrogen peroxide, and 2,2'-azobis(2-amidinopropane) dihydrochloride; active energy rays such as ultraviolet rays and electron rays. In addition, when oxidizable radical polymerization initiators are used, they may be used in combination with reducing agents, such as sodium sulfite, sodium hydrogen sulfite, ferrous sulfate, and L-ascorbic acid, to carry out redox polymerization. The amount of these polymerization initiators is usually in the range of 0.001 to 2 mol %, preferably, 0.01 to 0.5 mol %, of the aforementioned monomer component.

Water-absorbent resins, having various shapes such as amorphous pulverized shapes, spheres, fibers, sticks, approximate spheres, and flat shapes, resultant from the above-mentioned polymerization, can be used in the present invention. However, a preferable one has an average particle diameter of 200 to 600 $\mu$m, and a more preferable one contains particles of 150 $\mu$m or smaller in a ratio of 10% by weight or less, more preferably, 5% by weight or less.

In order to attain the object of the present invention, the amount of the flow of the eluting component out of the surface of an unsaturated swollen gel of a water-absorbent resin as obtained in the above-mentioned way needs to be reduced to 1 part by weight or less per 100 parts by weight of the water-absorbent resin. A water-absorbent resin of an absorption capacity of 40 (g/g) or more with a physiological salt solution usually contains eluting components such as water-soluble components, and as is well-known so far, these eluting components are extracted out of the gel by swelling to saturation the resin with a large amount of water or a large amount of a physiological salt solution. Where the water-absorbent resin is swollen in an unsaturated state under the below-mentioned conditions, however, the eluting components exude and migrate to the gel surface. The amount thereof is usually in the range of about 2 to about 20 parts by weight per 100 parts by weight of the water-absorbent resin although this amount does not necessarily have a correlation with the amount as extracted when swollen to saturation, because factors such as molecular weight, branching degree, or viscosity of eluting compounds have influence. However, the present inventors found that where the amount of the eluting component is large, the absorption efficiency under an increased pressure is not enhanced to a certain level or higher. That is to say, in order to attain the objective level of the absorption efficiency under an increased pressure in the present invention, the amount of the flow of the eluting component out of the surface of an unsaturated swollen gel of a water-absorbent resin needs to be reduced to an extremely low level of 1 part by weight or less, preferably, 0.5 parts by weight or less, more preferably, 0.1 parts by weight or less, per 100 parts by weight of the water-absorbent resin.

Examples of preferable methods for reducing the amount of the eluting component to such a low level include the following methods:

(1) a method in which the resultant water-absorbent resin is repeatedly brought into contact with treating solutions, such as water, organic solvents, and mixtures thereof, which can dissolve the eluting component, and these treating solutions and the resultant water-absorbent resin are then separated from each other; and (2) a method in which a water-absorbent resin is polymerized in the presence of a water-soluble chain transfer agent and then treated with a hydrophilic solution.

Although hydrophobic organic solvents can be used as the organic solvents in method (1) above, preferable examples of the organic solvents include the following hydrophilic organic solvents: lower alcohols such as methyl alcohol, ethyl alcohol, n-propyl alcohol, iso-propyl alcohol, n-butyl alcohol, iso-butyl alcohol, and t-butyl alcohol; ketones such as acetone; ethers such as dioxane and tetrahydrofuran; amides such as N,N-dimethylformamide ; sulfoxides such as dimethyl sulfoxide. In respect to effects of reducing the amount of the eluting component, however, it is preferable to use mixtures of water and organic solvents as the treating solutions, and in addition, it is the most preferable to use water alone as the treating solution.

In a more preferable embodiment, the composition of the treating solution is selected such that the water-absorbent resin can be swollen when the treating solution is repeatedly brought into contact with the resin. The swelling capacity of the water-absorbent resin during the treatment is preferably in the range of about 2 to about 500 (g/g), more preferably, about 5 to about 300 (g/g).

Although the amount of the treating solution as used in that case depends on the type or partide size of the water-absorbent resin, the optimal amount is usually in the range of 0.5 to 10,000,000 parts by weight, preferably, 5 to 500,000 parts by weight, per 1 part by weight of the solid content of the resin.

When the water-absorbent resin is brought into contact with the treating solution, the contacting can be carried out either in a continuous manner or in a discontinuous batch manner. A method is exemplified in which the water-absorbent resin is brought into contact with the treating solution, while stirring if necessary, and the resin is then separated from the treating solution by decantation or suction filtration. In addition, when the washing is carried out continuously, respective flow directions of the water-absorbent resin and the treating solution may be either parallel flows or counterflows and are not especially limited, but the parallel flows are preferable in respect to effects of reducing the amount of the eluting component. In addition, when the batch manner is carried out, the number of the treatments is not especially limited. The treatment temperature is in the range of 10 to 100° C., preferably, 20 to 60° C. After separated from the treating solution, the resin may further be dried if necessary, but caution is needed because there is a possibility that the amount of the eluting component as once reduced might increase due to factors such as the deterioration of the resin again.

In method (2) above, because the polymerization is carried out in the presence of a water-soluble chain transfer agent, the length per molecule of the resultant water-absorbent resin is relatively short. Therefore, the amount of the eluting component is relatively large in the stage the polymerization has ended, but the weight-average molecular weight of the eluting component is so low, for example, about 200,000 or less, that the eluting component can easily be removed by treating with a hydrophilic solution.

The water-soluble chain transfer agent as used in the present invention is not especially limited if it can dissolve in water or hydrophilic monomers, and examples thereof include thiols, thiol acids, secondary alcohols, amines, hypophosphorous acid (salts). Specifically, the following can be used: mercaptoethanol, mercaptopropanol, dodecylmercaptan, thioglycolic acid, thiomalic acid, 3-mercaptopropionic acid, isopropanol, hypophosphorous acid, formic acid, and salts thereof. One or more types selected from the group consisting of these compounds can be used, but hypophosphorous acid (salts), such as sodium hypophosphite, and thiols are preferably used in terms of effects thereof.

The amount of the water-soluble chain transfer agent, as used, depends on the type or amount of the water-soluble chain transfer agent as used or on the concentration of the aqueous hydrophilic-monomer solution, but the amount of the water-soluble chain transfer agent, as used, is preferably in the range of 0.001 to 1 mol %, more preferably, 0.005 to 0.3 mol %, of the hydrophilic monomer.

As to methods for reducing the amount of the eluting component other than methods (1) and (2) above, a method can also be exemplified in which the resultant water-absorbent resin is heated in the presence of a surface-crosslinking agent.

The surface-crosslinking agent, which can be used to heat in the presence thereof the water-absorbent resin which is obtained in the above-mentioned way and contains only a small amount of the eluting component, has a functional group that is reactive upon a functional group, for example, an acid group, of the water-absorbent resin, and conventional crosslinking agents as used for surface-crosslinking are exemplified below. Where the functional group of the water-absorbent resin is a carboxyl group, examples of the surface-crosslinking agent include one or more types selected from the group consisting of: polyhydric alcohol compounds such as ethylene glycol, diethylene glycol, propylene glycol, triethylene glycol, tetraethylene glycol, polyethylene glycol, 1,3-propanediol, dipropylene glycol, 2,2,4- trimethyl-1,3-pentanediol, polypropylene glycol, glycerol, polyglycerol, 2-butene-1,4-diol, 1,4-butanediol, 1,5-pentanediol, 1,6-hexanediol, 1,2-cyclohexanedimethanol, 1,2-cylohexanol, trimethylolpropane, diethanolamine, triethanolamine, polyoxypropylene, oxyethylene oxypropylene block copolymers, pentaerythritol, and sorbitol; polyepoxy compounds such as ethylene glycol diglycidyl ether, polyethylene diglycidyl ether, glycerol polyglycidyl ether, diglycerol polyglycidyl ether, polyglycerol polyglycidyl ether, propylene glycol diglycidyl ether, polypropylene glycol diglycidyl ether, and glycidol; polyamine compounds such as ethylenediamine, diethylenetriamine, triethylenetetramine, tetraethylenepentamine, pentaethylenehexamine, polyallylamine, and polyethyleneimine; polyisocyanate compounds such as 2,4-tolylene diisocyanate and hexamethylene diisocyanate; polyoxazoline compounds such as 1,2-ethylenebisoxazoline; alkylene carbonate compounds such as 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-,1, 3-dioxolan-2-one, 1,3-dioxan-2-one, 4-methyl-1,3-dioxan-2-one, and 4,6-dimethyl-1,3-dioxan-2-one; haloepoxy compounds such as epichlorohydrin, epibromohydrin, and α-methylepichlorohydrin; polyvalent metal compounds such as hydroxides and chlorides of zinc, calcium; magnesium, aluminum, iron, and zirconium. Preferable surface-crosslinking agents comprise at least one type selected from the group consisting of polyhydric alcohol compounds, polyamine compounds, polyepoxy compounds, and alkylene carbonate compounds.

These surface-crosslinking agents may be used alone or in combinations of two or more thereof. Where two or more surface-crosslinking agents are used, the surface-crosslinking can be carried out using the two or more surface-crosslinking agents separately in two or more steps, but on some occasions, it might be preferable to mix the two or more surface-crosslinking agents together at once because the water absorption capacity tends to decrease due to the surface-crosslinking treatment.

The amount of the surface-crosslinking agent as used in the present invention depends on its type or purpose, but the amount is usually in the range of 0.001 to 10 parts by weight, preferably, 0.01 to 5 parts by weight, per 100 parts by weight of the solid content of the water-absorbent resin according to the present invention. If the amount is within these ranges, a water-absorbing agent that is excellent in absorption capacity and absorption efficiency under an increased pressure can be obtained. An amount of the surface-crosslinking agent larger than 10 parts by weight is not only uneconomical but also tends to be excessive for attaining proper surface-crosslinking effects and might excessively reduce the absorption capacity. On the other hand, where the amount is smaller than 0.001 parts by weight, it might be difficult to obtain effects for enhancing the absorption properties under an increased pressure.

Apparatuses as used to mix the water-absorbent resin and the surface-crosslinking agent together in the present invention may be conventional ones, and examples thereof include cylinder type mixers, screw type mixers, screw type extruders, Turbulizers, Nauta type mixers, V-type mixers, ribbon type mixers, double arm type kneaders, flow type mixers, gas stream type mixers, rotatory disk type mixers, roll mixers, tumbling type mixers. The mixing speed may be either high or low.

When or after the water-absorbent resin and the surface-crosslinking agent are mixed together, water, steam, or aqueous solutions comprising water and hydrophilic organic solvents may further be added before carrying out a crosslinking reaction, because the absorption properties under an increased pressure might favorably greatly be improved by afterward adding water, steam, or the aqueous solutions in the case where the crosslinking agent, like polyhydric alcohols, polyepoxy compounds, and alkylene carbonate compounds, reacts with the water-absorbent resin through covalent bonding. Examples of the hydrophilic organic solvent as used in such a case include: lower alcohols such as methyl alcohol, ethyl alcohol, n-propyl alcohol, iso-propyl alcohol, n-butyl alcohol, iso-butyl alcohol, and t-butyl alcohol; ketones such as acetone; ethers such as dioxane and tetrahydrofuran; amides such as N,N-dimethylformamide; sulfoxides such as dimethyl sulfoxide. The optimal amount of water, as used in that case, depends on the type or particle size of the water-absorbent resin, but the optimal amount is usually in the range of 10 parts by weight or less, preferably, 1 to 5 parts by weight, per 100 parts by weight of the solid content of the resin. In addition, similarly, the amount of the hydrophilic organic solvent as used is usually in the range of 10 parts by weight or less, preferably, 0.1 to 5 parts by weight, per 100 parts by weight of the solid content of the resin.

In the present invention, after the water-absorbent resin and the surface-crosslinking agent are mixed together, the neighborhood of the surface of the water-absorbent resin is crosslinked by further carrying out a heating treatment as need arises depending on the type of the crosslinking agent.

Where the heating treatment is carried out in the present invention, the treatment temperature is preferably in the range of about 60 to about 230° C. Where the heating treatment temperature is lower than 60° C., the heating treatment might be time-consuming and therefore cause a reduction in productivity, and further, uniform crosslinking might not be achieved, so the objective resin of the present invention having high water absorption properties under an increased pressure might not be obtained. In addition, where the heating treatment temperature is higher than 230° C., the reduced amount of the eluting component might increase and it might be difficult to enhance the absorption efficiency under an increased pressure. The heating treatment temperature depends on the type of the crosslinking agent as used, but the heating treatment temperature is more preferably in the range of 80 to 200° C., still more preferably, 120 to 180° C.

The heating treatment can be carried out using conventional dryers or heating ovens, for example, channel type mixing and drying devices, rotary dryers, desk dryers, fluidized-bed dryers, gas stream type dryers, infrared dryers.

The production process (comprising the steps of: obtaining first a water-absorbent resin, which has an absorption capacity of a specific value or more and of which the amount of the eluting component, flowingout of the surface of an unsaturated swollen gel, is reduced to a specific value or less; and then crosslinking the surface of the resin) is explained above as a process for obtaining the present water-absorbing agent that is excellent both in the absorption capacity under an increased pressure and in the absorption efficiency under an increased pressure. However, a process for obtaining the water-absorbing agent of the present invention is not limited to the above-mentioned production process. For example, the water-absorbing agent can also be obtained by a process comprising the step of crosslinking the neighborhood of the surface of a particle of a specific particle size range in a specific manner to give the particle a specific crosslinking density gradient Hereinafter, this manner is explained.

That is to say, the water-absorbing agent of the present invention can also be obtained in the following manner: the particle diameter of a water-absorbent resin, as preferably obtained by aqueous solution polymerization, is adjusted so as to substantially fall within the range of from 106 μm to less than 500 μm by operations such as classification; and the resin is then heated in the presence of two or more surface-crosslinking agents of different solubility parameter ranges.

The phrase "to substantially fall within the range of from 106 μm to less than 500 μm," referred to herein, means that particles within the particle size range of from 106 μm to less than 500 μm comprise the major percentage by weight of all particles of the water-absorbent resin. The major percentage by weight is preferably 90 wt % or more, further preferably, 95 wt % or more.

The above-mentioned water-absorbent resin may be granulated to predetermined shapes and may have various shapes such as spheres, scales, amorphous pulverized shapes, and granules. In addition, the water-absorbent resin may comprise either a primary particle or a granulated material of primary particles. Where the particle diameter is not substantially within the range of from 106 μm to less than 500 μm, it is difficult to obtain the water-absorbing agent having excellent properties such as absorption efficiency under an increased pressure.

If a water-absorbent resin, as obtained by polymerizing acrylic acid as the monomer and neutralizing the resultant polymer gel afterward, is used as the above-mentioned water-absorbent resin, a water-absorbing agent having more excellent absorption capacity, absorption efficiency and absorption capacity of a lower swollen gel layer under an increased pressure can be obtained.

In addition, the above-mentioned solubility parameter is a value that is commonly used as a factor showing the polarity of a compound. As to the solubility parameter, values of solubility parameters $\delta[(cal/cm^3)^{1/2}]$ of solvents as disclosed on pages 527–539 of *Polymer Handbook*, 3rd edition (published by WILEY INTERSCIENCE PUBLISHING CO., LTD.) are applied to the present invention. In addition, as to solubility parameters of solvents that are not disclosed in the above-cited pages, a value that is obtained by substituting Hoy's cohesive energy constant (as disclosed on page 525 of the above-mentioned *Polymer Handbook*) into Small's equation (as disclosed on page 524 of the *Polymer Handbook*) is applied.

As to the two or more surface-crosslinking agents of different solubility parameter ranges, a first surface-crosslinking agent has a solubility parameter (SP value) of 12.5 to 15.0 $[(cal/cm^3)^{1/2}]$ and can react with a carboxyl group, and a second surface-crosslinking agent has a solubility parameter of less than 12.5 $[(cal/cm^3)^{1/2}]$ and can react with a carboxyl group. Although not clear, the reason why the water-absorbing agent having excellent absorption capacity and absorption efficiency under an increased pressure is obtained by combining the first and second surface-crosslinking agents having different solubility parameters from each other seems to be that the permeation of the crosslinking agents into the surface of the water-absorbent resin or the thickness of the crosslinking is controlled.

Specific examples of the first surface-crosslinking agent include ethylene glycol, propylene glycol, ethylene carbonate, and propylene carbonate, and one or more types selected from the group consisting of these compounds can be used. In addition, specific examples of the second surface-crosslinking agent include diethylene glycol, triethylene glycol, tetraethylene glycol, dipropylene glycol, 1,3-butanediol, 1,4-butanediol, 1,5-pentanediol, ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, diethylenetriamine, triethylenetetramine, and epichlorohydrin, and one or more types selected from the group consisting of these compounds can be used.

The first and second surface-crosslinking agents can be used separately, but in terms of the simplicity it is preferable to use them simultaneously.

The amount of the surface-crosslinking agent as used depends on the compounds or combinations thereof used as the surface-crosslinking agent, but the amount of the first surface-crosslinking agent is preferably in the range of 0.01 to 5 parts by weight, more preferably, 0.1 to 2 parts by weight, per 100 parts by weight of the solid content of the water-absorbent resin, and the amount of the second surface-crosslinking agent is preferably in the range of 0.001 to 1 part by weight, more preferably, 0.005 to 0.5 parts by weight, per 100 parts by weight of the solid content of the water-absorbent resin. The use of too large an amount of the surface-crosslinking agent is unfavorably uneconomical. In addition, where the amount of the surface-crosslinking agent is too small, it is unfavorably difficult to obtain effects for enhancing the absorption efficiency under an increased pressure with regard to the water-absorbent resin.

When the water-absorbent resin and the surface-crosslinking agent are mixed together, it is preferable to use water as the solvent. The amount of water as used depends on the type or particle size of the water-absorbent resin, but the amount is preferably in the range of from more than 0 parts by weight to not more than 20 parts by weight, and more preferably, in the range of 0.5 to 10 parts by weight, per 100 parts by weight of the solid content of the water-absorbent resin.

In addition, when the water-absorbent resin and the surface-crosslinking agent are mixed together, a hydrophilic organic solvent may be used as the solvent if necessary. Examples of the hydrophilic organic solvent include: lower alcohols such as methyl alcohol, ethyl alcohol, n-propyl alcohol, isopropyl alcohol, n-butyl alcohol, isobutyl alcohol, and t-butyl alcohol; ketones such as acetone; ethers such as dioxane and tetrahydrofuran; amides such as N,N-dimethylformamide; sulfoxides such as dimethyl sulfoxide. The amount of the hydrophilic organic solvent as used depends on the type or particle size of the water-absorbent resin, but the amount is preferably in the range of 20 parts by weight or less, more preferably, 0.1 to 10 parts by weight, per 100 parts by weight of the solid content of the resin.

When the water-absorbent resin and the surface-crosslinking agent are mixed together, the water-absorbent resin, for example, may be dispersed into the above-mentioned hydrophilic organic solvent, and then the surface-crosslinking agent may be mixed into the resultant dispersion. However, the mixing method is not especially limited. In a preferable one of various mixing methods, the surface-crosslinking agent, as dissolved in either or both of water and the hydrophilic organic solvent as need arises, is directly sprayed or dropped to the water-absorbent resin, thus mixing the water-absorbent resin and the surface-crosslinking agent together. In addition, where the mixing is carried out using water, a water-insoluble fine particle powder or a surfactant may be allowed to coexist.

Mixing apparatuses, as used to mix the water-absorbent resin and the surface-crosslinking agent together, preferably have great mixing force to uniformly and surely mix the reactants together. Preferable examples of such apparatuses include cylinder type mixers, double-wall cone type mixers, V-character type mixers, ribbon type mixers, screw type mixers, fluidized-oven rotary disk type mixers, gas stream type mixers, double arm type kneaders, internal mixers, pulverizing type mixers, rotatory mixers, screw type extruders.

After the water-absorbent resin and the surface-crosslinking agent are mixed together, the neighborhood of the surface of the water-absorbent resin is crosslinked by carrying out a heating treatment. Although the treatment temperature of the heating treatment depends on the surface-crosslinking agent as used, the treatment temperature is generally in the range of 90 to 250° C. Where the treatment temperature is lower than 90° C., no uniform crosslinking structure is formed, and therefore, the water-absorbing agent with excellent properties such as diffusion absorption capacity unfavorably cannot be obtained. Where the treatment temperature is higher than 250° C., a deterioration of the water-absorbing agent is caused, and therefore, the performance of the water-absorbing agent unfavorably becomes bad. The heating treatment temperature is more preferably in the range of 160 to 250° C.

The above-mentioned heating treatment can be carried out using conventional dryers or heating ovens. Examples of the dryers include channel type mixing and drying devices, rotary dryers, desk dryers, fluidized-bed dryers, gas stream type dryers, infrared dryers.

The water-absorbing agent of the present invention, as obtained in the above-mentioned way, is as follows: water-absorbing agent (1), which has an absorption capacity of 30 (g/g) or more under an increased pressure and an absorption efficiency of 0.7 or more under an increased pressure, wherein the absorption efficiency under an increased pressure is defined as a ratio between absorption capacities in directions of the height of a swollen gel in the measurement of the absorption capacity; and/or water-absorbing agent (2), which has an absorption capacity of 45 (g/g) or more under an increased pressure with regard to a lower layer near a liquid-absorbing portion of the swollen gel after the above-mentioned measurement, and which has the above-mentioned absorption efficiency of 0.4 or more under an increased pressure. The ratio between absorption capacities in the direction of the height of a swollen gel is a ratio between an absorption capacity of the gel at a layer portion in the neighborhood of a portion contacting a liquid and an absorption capacity of the gel at a layer portion, which does not directly contact the liquid and is the farthest from the liquid, in a state where the gel is swollen in layered form under an increased pressure. In the present invention, this ratio is defined as a ratio of an absorption capacity of an upper swollen gel layer, which is far from a liquid-absorbing portion, to an absorption capacity of a lower swollen gel layer, which is near the liquid-absorbing portion, after the below-mentioned measurement of the absorption capacity under an increased pressure is made, and furthermore, that ratio may be called the absorption efficiency under an increased pressure.

Conventionally known water-absorbent resins merely have an absorption efficiency, as defined as the ratio between absorption capacities in directions of the height of a swollen gel, of at most about 0.5 to about 0.6 under an increased pressure even if those resins have high absorption capacity under an increased pressure. Water-absorbing agent (1) above, according to the present invention, displays an absorption efficiency, as defined as the ratio between absorption capacities in the direction of the height of a swollen gel, of 0.70 or more, preferably, 0.75 or more, under an increased pressure, wherein this is a high value that has not been obtained so far, and the water-absorbing agent of the present invention further has a high absorption capacity of 30 (g/g) or more, preferably, 35 (g/g) or more, under an increased pressure.

In addition, conventionally known water-absorbent resins usually merely have an absorption capacity of a lower swollen gel layer of at most about 35 to about 40 (g/g) under an increased pressure, and no conventional water-absorbent resins have an absorption capacity of a lower swollen gel layer of more than 45 (g/g). Water-absorbing agent (2) above, according to the present invention, however, displays a very high value of the absorption capacity of the lower swollen gel layer, namely, 45 (g/g) or more, under an increased pressure and therefore further has a high absorption capacity under an increased pressure as a whole of the water-absorbing agent if the water-absorbing agent has a relatively high absorption efficiency of 0.4 or more.

The present invention further provides water-absorbing agent (3), wherein the water-absorbing agent, having a high absorption capacity under an increased pressure as a whole of the water-absorbing agent, is defined from a relationship between the absorption efficiency and the absorption capacity of the lower swollen gel layer under an increased pressure. That is to say, if the relationship between the absorption efficiency and the absorption capacity of the lower swollen gel layer under the increased pressure is defined by the following equation:

absorption efficiency under increased pressure>$1.82-2.93\times10^{-2}\times$ (absorption capacity of lower swollen gel layer under increased pressure), the absorption capacity under the increased pressure is high as a whole of the water-absorbing agent. However, where the absorption capacity of the lower swollen gel layer is extremely low, the absorption capacity is low as a whole of the water-absorbing agent even if the absorption efficiency is high. Therefore, the lower limit of the absorption capacity of the lower swollen gel layer is defined as 30 (g/g). Similarly, where the absorption efficiency is extremely low, the absorption capacity is low as a whole of the water-absorbing agent even if the absorption capacity of the lower swollen gel layer is high. Therefore, the lower limit of the absorption efficiency is defined as 0.3.

The water-absorbing agent of the present invention has not only excellent absorption properties under an increased pressure but also properties in which: there is only a small difference between swelling capacities at upper and lower positions in a swollen gel layer, and the resin can swell so uniformly that inherent absorbency of the resin can be displayed. As to this water-absorbing agent, the entirety of the resin can be used with very good efficiency. Accordingly, even where used for thin type absorbent articles (e.g. disposable diapers) containing water-absorbent resins of high concentration, the water-absorbing agent of the present invention displays excellent absorption capacity and absorption efficiency under a high load. Therefore, the amount of liquids, as absorbed until leaking, is enhanced. (Effects and Advantages of the Invention):

The water-absorbing agent and the production process therefor, according to the present invention, can provide a water-absorbing agent that has high absorption capacity under an increased pressure and is excellent in the absorption efficiency under an increased pressure.

Accordingly, when the water-absorbent resin is used under high concentration conditions of 50 wt % or more (ratio to the sum total of the water-absorbent resin and fibrous materials such as pulp) in water-absorbent articles, such as disposable diapers and sanitary napkins, as obtained by combining the water-absorbent resin with fibrous materials, the water-absorbing agent of the present invention can display sufficient absorbency even if a heavier load is applied, and in addition, the water-absorbing agent of the present invention has properties in which there is only a small difference between swelling capacities at upper and lower positions in a swollen gel layer and in which the resin can swell so uniformly that inherent absorbency of the resin can be displayed, and further, the entirety of the resin can be used with very good efficiency. Therefore, the invention can reduce the amount of the resin as used, and can provide further thinned absorbent articles. Furthermore, the water-absorbing agent of the present invention can favorably be used for various purposes, for example, for humor absorbent articles (e.g. injury-protecting materials, injury-healing materials), drip absorbent materials for food, freshness-maintaining materials for food, water-cutoff materials, and soil water-holding materials.

DETAILED DESCRIPTION OF THE PREFERRED EMBODIMENTS

Hereinafter, the present invention is more specifically illustrated by the following examples of some preferred embodiments in comparison with comparative examples not according to the invention. However, the present invention is not limited to the below-mentioned examples. In addition, in the present invention, the performance of the water-absorbing agent was measured by the following methods:

(a) Absorption Capacity

A nonwoven fabric bag (60 mm×60 mm), in which 0.2 g of water-absorbing agent was put uniformly, was immersed into a 0.9 wt % aqueous sodium chloride solution (physiological salt solution). After 60 minutes, the bag was drawn up and then drained at 250 G with a centrifuge for 3 minutes. Then, weight $W_1$ (g) of the bag was measured. In addition, the same procedure as mentioned above was carried out using no water-absorbing agent, and weight $W_0$ (g) of the resultant bag was measured. Thus, the absorption capacity (g/g) was calculated from these weights $W_1$ and $W_0$ in accordance with the following equation:

absorption capacity (g/g)=(weight $W_1$(g)−weight $W_0$(g))/(weight (g) of water-absorbing agent).

(b) Absorption Capacity Under Increased Pressure

Hereinafter, first, a measurement apparatus as used for measuring the absorption capacity under increased pressure is simply explained while referring to FIG. 1.

As is shown in FIG. 1, the measurement apparatus comprises: a scale 1; a vessel 2 of a predetermined capacity as mounted on the scale 1; an air-inhaling pipe 3; an introducing tube 4, a glass filter 6; and a measurement part 5 as mounted on the glass filter 6. The vessel 2 has an opening part 2a on the top and an opening part 2b on the side. The air-inhaling pipe 3 is inserted through the opening part 2a, and the introducing tube 4 is fitted to the opening part 2b. In addition, the vessel 2 contains a predetermined amount of artificial urine 11 (composition: an aqueous solution containing sodium sulfate of 0.2 wt %, potassium chloride of 0.2 wt %, magnesium chloride hexahydrate of 0.05 wt %, calcium chloride dihydrate of 0.025 wt %, ammonium dihydrogen phosphate of 0.085 wt %, and diammonium hydrogen phosphate of 0.015 wt %). The lower part of the air-inhaling pipe 3 is submerged in the artificial urine 11. The glass filter 6 is formed in a diameter of 70 mm. The vessel 2 and the glass filter 6 are connected to each other through the introducing tube 4. In addition, the upper part of the glass filter 6 is fixed so as to be located a little higher than the lower end of the air-inhaling pipe 3.

The measurement part 5 comprises: a filter paper 7; a supporting cylinder 8; a metal net 9 as attached to the bottom of the supporting cylinder 8; and a weight 10; and the measurement part 5. formed by mounting the filter paper 7 and the supporting cylinder 8 (i.e. metal net 9) in this order on the glass filter 6 and further mounting the weight 10 inside the supporting cylinder 8, namely, on the metal net 9. The supporting cylinder 8 is formed in an inner diameter of 60 mm. The metal net 9 is made of stainless steel and formed in 400 mesh (mesh size: 38 µm). An arrangement is made such that a predetermined amount of water-absorbing agent can uniformly be spread on the metal net 9. The weight 10 is adjusted in weight such that a load of 50 g/cm$^2$ can uniformly be applied to the metal net 9, namely, to the water-absorbing agent.

The absorption capacity under an increased pressure was measured with the measurement apparatus having the above-mentioned constitution. The measurement method is hereinafter explained.

First, predetermined preparatory operations were made, in which, for example, a predetermined amount of the artificial urine 11 was placed into the vessel 2, and the air-inhaling pipe 3 was inserted into the vessel 2. Next, the filter paper 7 was mounted on the glass filter 6. On the other hand, in parallel with these mounting operations, 0.9 g of water-absorbing agent was uniformly spread inside the supporting cylinder, namely, on the metal net 9, and the weight 10 was put on the water-absorbing agent.

Next, the metal net 9, namely, the supporting cylinder 8 (in which the water-absorbing agent and the weight 10 were put) was mounted on the filter paper 7.

Then, weight $W_2$ (g) of the artificial urine 11, as absorbed into the water-absorbing agent over a period of 60 minutes since the supporting cylinder 8 had been mounted on the filter paper 7, was measured with the scale 1.

Then, the absorption capacity (g/g) under an increased pressure after 60 minutes from the initiation of the absorption was calculated from weight $W_2$ in accordance with the following equation:

absorption capacity (g/g) under increased pressure=(weight $W_2$ (g))/(weight (g) of water-absorbing agent).

(c) Absorption Efficiency Under Increased Pressure

Immediately after the above-mentioned measurement of the absorption capacity under an increased pressure had been carried out, the measurement part 5 was removed from the measurement apparatus for the absorption capacity under an increased pressure (i.e. from the filter paper 7) in a state where the water-absorbing agent (swollen gel) as swollen due to the absorption of the artificial urine was present inside the supporting cylinder 8 and where the weight 10 was put on the water-absorbing agent. The removed measurement part 5 was left on a pile of ten pieces of filter paper of 90 mm in diameter (Qualitative filter paper No. 2, made by Toyo Roshi Kaisha, Ltd.) for 2 minutes, thus removing the artificial urine (clearance artificial urine as unabsorbed into the water-absorbing agent) which was present inside the supporting cylinder and between particles of the swollen gel. Then, weight $W_3$ (g) was measured in a state where the swollen gel was present inside the supporting cylinder and where the weight 10 was put on the gel. Weight $W_4$ (g) of the supporting cylinder 8 and weight $W_5$ (g) of the weight 10, as both measured beforehand, were subtracted from $W_3$ (g) to determine weight $W_6$ (g) of the swollen gel of after the removal of the clearance artificial urine.

Next, the weight 10 was removed from the supporting cylinder, and the swollen gel was retrieved from inside the supporting cylinder every one-third of weight $W_6$ (g) of the swollen gel from the top, thus obtaining upper, intermediate, and lower layers of the swollen gel. The upper layer of the retrieved gel was weighed out onto an aluminum cup and dried at 180° C. for 3 hours, and absorption capacity $G_1$ (g/g) of the upper layer of the gel was determined from the weight of the resultant dried product, when the absorption capacity of the gel was calculated assuming that 50% of the artificial urine component had been taken into the absorbing agent.

The same procedure as the above-mentioned was carried out for the lower layer of the retrieved gel to determine absorption capacity $G_2$ (g/g) of the lower layer of the gel.

Then, the absorption efficiency under an increased pressure was calculated in accordance with the following equation:

$$\text{absorption efficiency under increased pressure} = G_1/G_2.$$

(d) Amount of Eluting Component

The amount of the eluting component is measured by different methods depending on crosslinked products of partially neutralized polyacrylic acid and other water-absorbent resins. A colloid titration method is applied to the crosslinked products pf partially neutralized polyacrylic acid, and a weight measurement method is applied to the other water-absorbent resins.

* Colloid titration method:

1.000 (g) of water-absorbent resin was added to 25 (g) of a 0.9 wt % aqueous sodium chloride solution to swell the resin uniformly. After 1 hour, the swollen water-absorbent resin was dispersed into 975 g of deionized water, stirred for 1 minute, and then filtered with filter paper. Next, 50 (g) of the resultant filtrate was placed into a 100 ml beaker, and 1 ml of a 0.1 N aqueous sodium hydroxide solution, 10.00 ml of an N/200 aqueous methyl glycol chitosan solution, and 4 drop of a 0.1 wt % aqueous Toluidine Blue solution were added to the filtrate.

Next, the resultant solution in the beaker was subjected to colloid titration with an N/400 aqueous potassium polyvinyl sulfate solution to determine titration amount A (ml) assuming that the moment at which the color of the solution had changed from blue to red purple was the terminal of the titration. In addition, titration amount B (ml) was determined by carrying out blank titration in the same way as mentioned above, except that 50 (g) of the filtrate was replaced with 50 (g) of deionized water. Then, the amount of the eluting component (wt %) was calculated from titration amounts A and B and from neutralization ratio×(mol %) of the polyacrylic acid, as used as the water-absorbent resin, in accordance with the following equation:

$$\text{amount of eluting component (wt \%)} = (B \text{ (ml)} - A \text{ (ml)}) \times 0.005 \times [72.(100-x) + 94x]/100.$$

* Weight measurement method:

1.000 (g) of water-absorbent resin was added to 25 (g) of a 0.9 wt % aqueous sodium chloride solution to swell the resin uniformly. After 1 hour, the swollen water-absorbent resin was dispersed into 975 g of deionized water, stirred for 1 minute, and then filtered with filter paper. Next, 50 (g) of the resultant filtrate was dried, and the solid content was measured to calculate the amount of the eluting component (wt %) in accordance with the following equation:

$$\text{amount of eluting component (wt \%)} = ((\text{solid content in 50 (g) of filtrate) (wt \%)} - (\text{NaCl content in 50 (g) of filtrate) (wt \%)}) \times 20.$$

(e) Molecular Weight of Eluting Component:

The weight-average molecular weight of the eluting component as sampled in method (d) above was determined by gel permeation chromatography using 12 types of commercially available sodium polyacrylates, of which the respective molecular weights were known peak molecular weights (Mp): 1,100,000; 782,200; 467,300; 392,600; 272,900; 193800; 115,000; 28,000; 16,000; 7,500; 2,950; 1,250), as the standard.

(f) Evaluation as to Absorbent Articles (Kewpie Doll Test)

Seventy-five parts by weight of a water-absorbing agent and 25 parts by weight of wood-pulverized pulp were mixed together in a dry manner with a mixer. Next, the resultant mixture was shaped into a web of the size of 120 mm×350 mm by pneumatically molding the mixture on a wire screen of 400 mesh (mesh size: 38 μm) with a batch type pneumatic device. In addition, this web was pressed for 5 seconds under a pressure of 2 kg/cm², thus obtaining an absorbent material of a weight of about 500 g/m².

Next, a back sheet (liquid-unpermeable sheet) of a liquid-unpermeable polypropylene with a so-called leg gather, the above-mentioned absorbent materials, and a top sheet (liquid-permeable sheet) of a liquid-permeable polypropylene were attached to each other in this order with double coated tapes, and two-so-called tape fasteners were then provided to the resultant attached product, thus obtaining an absorbent article (i.e. disposable diaper). The weight of this absorbent article was 44 g.

This absorbent article was fitted on each of three so-called kewpie dolls (body length: 55 cm, weight: 5 kg), and these dolls were laid on their faces. Then, a tube was inserted between the absorbent article and the dolls, and 70 ml of a physiological salt solution was injected through the tube every 20 minutes to a position corresponding to where urine is discharged by the human body. This injection operation was ended when the injected physiological salt solution began leaking without being absorbed by the absorbent article, and the number of injections that had been made until that time was counted.

Referential Example 1

A reaction solution was prepared by dissolving 3.56 g of polyethylene glycol diacrylate into 5,500 g of an aqueous solution of sodium acrylate with a neutralization ratio of 75 mol % (monomer concentration: 33 wt %). Next, this solution was degassed under a nitrogen gas atmosphere for 30 minutes, and then supplied into a reaction vessel as prepared by capping a stainless-steel-made double arm type kneader of a capacity of 10 liters having two sigma type wings and a jacket. While maintaining the reaction solution at 30° C., the atmosphere inside the system was replaced with a nitrogen gas. Next, while stirring the reaction solution, 2.4 g of ammonium persulfate and 0.12 g of L-ascorbic acid were added, so that a polymerization reaction started about 1 minute later. The polymerization was carried out at 30–80° C., and the resultant hydrogel polymer was separated out after 60 minutes from the initiation of the polymerization.

The resultant hydrogel polymer had a finely divided diameter of about 5 mm. This finely divided hydrogel polymer was spread on a 50-mesh metal net and dried at 150° C. with hot air for 90 minutes. Then, the resultant dried product was pulverized with a vibration mill and further classified with a sieve, thus obtaining water-absorbent resin (a) having a particle diameter within the range of from 300 μm to less than 600 μm.

This resin had an absorption capacity of 58 (g/g) and an amount of the eluting component of 5.5 (wt %). The weight-average molecular weight of the eluting component was 350,000.

Referential Example 2

Three nylon bags (20×30 cm) of 100 mesh, containing 3 (g) of water-absorbent resin (a) as obtained in Referential Example 1, respectively, were prepared, placed into a pipette washer of a capacity of about 16 liters, and left under a deionized water flow of 1.6 liters/min for 1 day.

Then, the swollen water-absorbent resin was taken out of the nylon bags, dried at 80° C. with hot air for 24 hours, and classified with a sieve, thus obtaining water-absorbent resin (b) having a particle diameter within the range of from 300 μm to less than 600 μm.

This resin had an absorption capacity of 57 (g/g), an amount of the eluting component of 0.5 (wt %), and a water content of 5.7 (wt %).

Referential Example 3

Water-absorbent resin (c) having a particle diameter within the range of from 300 μm to less than 600 μm was obtained in the same way as of Referential Example 2 except that the step of leaving the resin under a deionized water flow of 1.6 liters/min for 1 day was replaced with the step of leaving the resin under a deionized water flow of 1.6 liters/min for 7 days.

The resultant resin had an absorption capacity of 56 (g/g), an amount of the eluting component of 0.1 (wt %), and a water content of 5.8 (wt %).

EXAMPLE 1

A surface-crosslinking agent comprising 0.03 parts by weight of glycerol, 0.05 parts by weight of ethylene glycol diglycidyl ether, 3 parts by weight of water, 5 parts by weight of isopropyl alcohol, and 0.5 parts by weight of lactic acid was mixed with 100 parts by weight of water-absorbent resin (b) as obtained in Referential Example 2. The resultant mixture was heated at 180° C. for 20 minutes, thus obtaining water-absorbing agent (1) according to the present invention. As to water-absorbing agent (1), Table 1 shows results of: the absorption capacity; the absorption capacity under an increased pressure; the absorption capacity of the upper swollen gel layer under the increased pressure; the absorption capacity of the lower swollen gel layer under the increased pressure; the absorption efficiency under the increased pressure; and the kewpie doll test.

EXAMPLE 2

A surface-crosslinking agent comprising 0.03 parts by weight of glycerol, 0.05 parts by weight of ethylene glycol diglycidyl ether, 3 parts by weight of water, 5 parts by weight of isopropyl alcohol, and 0.5 parts by weight of lactic acid was mixed with 100 parts by weight of water-absorbent resin (c) as obtained in Referential Example 3. The resultant mixture was heated at 120° C. for 15 minutes, thus obtaining water-absorbing agent (2) according to the present invention. As to water-absorbing agent (2), Table 1 shows results of: the absorption capacity; the absorption capacity under an increased pressure; the absorption capacity of the upper swollen gel layer under the increased pressure; the absorption capacity of the lower swollen gel layer under the increased pressure; the absorption efficiency under the increased pressure; and the kewpie doll test.

Comparative Example 1

A surface-crosslinking agent comprising 0.03 parts by weight of glycerol, 0.05 parts by weight of ethylene glycol diglycidyl ether, 3 parts by weight of water, 5 parts by weight of isopropyl alcohol, and 0.5 parts by weight of lactic acid was mixed with 100 parts by weight of water-absorbent resin (a) as obtained in Referential Example 1. The resultant mixture was heated at 180° C. for 20 minutes, thus obtaining comparative water-absorbing agent (1) not according to the present invention. As to comparative water-absorbing agent (1), Table 1 shows results of: the absorption capacity; the absorption capacity under an increased pressure; the absorption capacity of the upper swollen gel layer under the increased pressure; the absorption capacity of the lower swollen gel layer under the increased pressure; the absorption efficiency under the increased pressure; and the kewpie doll test.

Comparative Example 2

A surface-crosslinking agent comprising 0.7 parts by weight of glycerol, 0.1 parts by weight of ethylene glycol diglycidyl ether, 4 parts by weight of water, 5 parts by weight of isopropyl alcohol, and 1 part by weight of lactic acid was mixed with 100 parts by weight of water-absorbent resin (a) as obtained in Referential Example 1. The resultant mixture was heated at 180° C. for 50 minutes, thus obtaining comparative water-absorbing agent (2) not according to the present invention. As to comparative water-agent (2), agent (2), Table 1 shows results of: the absorption capacity; the absorp capacity under an increased pressure; the absorption capacity of the upper swollen gel layer under the increased pressure; the absorption capacity of the lower swollen gel layer under the increased pressure; the absorption efficiency under the increased pressure; and the kewpie doll test.

Referential Example 4

A reaction solution was prepared by dissolving 23.43 g of polyethylene glycol diacrylate and 5.79 g of sodium hypophosphite monohydrate into 5,500 g of an aqueous solution of sodium acrylate with a neutralization ratio of 75 mol % (monomer concentration: 39 wt %). Next, this solution was degassed under a nitrogen gas atmosphere for 30 minutes, and then supplied into the same reaction vessel as that used in Referential Example 1. While maintaining the reaction solution at 30° C., the atmosphere inside the system was replaced with a nitrogen gas. Next, while stirring the reaction solution, 2.4 g of ammonium persulfate and 0.12 g of L-ascorbic acid were added, so that a polymerization reaction started about 1 minute later. The polymerization was carried out at 30–80° C., and the resultant hydrogel polymer was separated out after 60 minutes from the initiation of the polymerization.

The resultant hydrogel polymer had a finely divided diameter of about 5 mm. This finely divided hydrogel polymer was spread on a 50-mesh metal net and dried at 150° C. with hot air for 90 minutes. Then, the resultant dried product was pulverized with a vibration mill and further classified with a sieve, thus obtaining water-absorbent resin (d) having a particle diameter within the range of from 300 μm to less than 600 m. This resin had an absorption capacity of 48 (g/g), an amount of the eluting component of 11.7 (wt %), and a weight-average molecular weight of the eluting component of 120,000.

Three nylon bags (20×30 cm) of 100 mesh, containing 3 (g) of the resultant water-absorbent resin (d), respectively, were prepared, placed into a pipette washer of a capacity of about 16 liters, and left under a deionized water flow of 1.6 liters/min for 1 day. Then, the swollen water-absorbent resin was taken out of the nylon bags, dried at 80° C. with hot air for 24 hours, and classified with a sieve, thus obtaining water-absorbent resin (e) having a particle diameter within the range of from 300 μm to less than 600 μm.

This resin had an absorption capacity of 51 (g/g) and an amount of the eluting component of 0.1 (wt %).

EXAMPLE 3

A surface-crosslinking agent comprising 0.1 parts by weight of ethylene glycol diglycidyl ether, 1 part by weight of propylene glycol, 3 parts by weight of water, and 2 parts by weight of isopropyl alcohol was mixed with 100 parts by weight of water-absorbent resin (e) as obtained in Referential Example 4. The resultant mixture was heated at 120° C. for 15 minutes, thus obtaining water-absorbing agent (3) according to the present invention. As to water-absorbing agent (3), Table 1 shows results of: the absorption capacity; the absorption capacity under an increased pressure; the absorption capacity of the upper swollen gel layer under the increased pressure; the absorption capacity of the lower swollen gel layer under the increased pressure; the absorption efficiency under the increased pressure; and the kewpie doll test.

Referential Example 5

A reaction solution was prepared by dissolving 4.96 g of polyethylene glycol diacrylate into 5,500 g of an aqueous solution of sodium acrylate with a neutralization ratio of 75 mol % (monomer concentration: 33 wt %). Next, this solution was degassed under a nitrogen gas atmosphere for 30 minutes, and then supplied into a reaction vessel as prepared by capping a stainless-steel-made double arm type kneader of a capacity of 10 liters having two sigma type wings and a jacket. While maintaining the reaction solution at 30° C., the atmosphere inside the system was replaced with a nitrogen gas. Next, while stirring the reaction solution, 2.46 g of sodium persulfate and 0.10 g of L-ascorbic acid were added, so that a polymerization reaction started about 1 minute later. The polymerization was carried out at 30–80° C., and the resultant hydrogel polymer was separated out after 60 minutes from the initiation of the polymerization.

The resultant hydrogel polymer had a finely divided diameter of about 5 mm. This finely divided hydrogel polymer was spread on a 50-mesh metal net and dried at 150° C. with hot air for 90 minutes. Then, the resultant dried product was pulverized with a vibration mill and further classified with a sieve, thus obtaining water-absorbent resin (f) of which 98 wt % comprised particles with a particle diameter range of from 106 μm to less than 500 μm.

Referential Example 6

An aqueous acrylic acid solution, as prepared by mixing homogeneously 160.0 parts by weight of acrylic acid, 622.5 parts by weight of ion-exchanged water, and 0.342 parts by weight of N,N'-methylenebisacrylamide, was placed into a cylindrical vessel and degassed under a nitrogen gas atmosphere. Next, while maintaining the acrylic add solution at 15° C., 9.6 parts by weight of a 5 wt % aqueous solution of 2,2'-azobis (2-amidinopropane) dihydrochloride (trade name: V-50, made by Wako Pure Chemical Industries, Ltd.), 4.57 parts by weight of a 3.5 wt % aqueous hydrogen peroxide solution, and 4.0 parts by weight of a 1 wt % aqueous L-ascorbic acid solution were added and mixed as polymerization initiators into the acrylic acid solution, so that a polymerization reaction started about 1 minute later. Then, stationary adiabatic polymerization was continued for 1.5 hours, and the resultant hydrogel polymer was separated from the reaction vessel and then placed into a kneader with a jacket of 70° C., and then the blade of the kneader was stirred for 20 minutes, thus dividing finely the hydrogel into particles about 1 to about 5 mm. Thereafter, the hydrogel was neutralized with 1024.6 parts by weight of a 6.5 wt % aqueous sodium hydroxide solution. The hydrogel was uniformly neutralized when the color of phenolphthalein, as used as the indicator, had entirely disappeared. Furthermore, the neutralized hydrogel was dried with a hot air dryer of 160° C. for 1 hour, and then pulverized with a portable pulverizer, and then classified with a sieve, thus obtaining water-absorbent resin (g) of which 97 wt % comprised particles with a particle diameter range of from 106 μm to less than 500 μm. The neutralization ratio of this water-absorbent resin was 75 mol %.

Referential Example 7

An aqueous acrylic acid solution, as prepared by mixing homogeneously 160.0 parts by weight of acrylic acid, 622.5 parts by weight of ion-exchanged water, and 0.342 parts by weight of N,N'-methylenebisacrylamide, was placed into a cylindrical vessel and degassed under a nitrogen gas atmosphere. Next, while maintaining the acrylic acid solution at 15° C., 9.6 parts by weight of a 5 wt % aqueous solution of 2,2'-azobis(2-amidinopropane) dihydrochloride (trade name: V-50, made by Wako Pure Chemical Industries, Ltd.), 4.57 parts by weight of a 3.5 wt % aqueous hydrogen peroxide solution, and 4.0 parts by weight of a 1 wt % aqueous L-ascorbic acid solution were added and mixed as polymerization initiators into the acrylic acid solution, so that a polymerization reaction started about 1 minute later. Then, stationary adiabatic polymerization was continued for 1.5 hours, and the resultant hydrogel polymer was separated from the reaction vessel and then placed into a kneader with a jacket of 70° C., and then the blade of the kneader was stirred for 20 minutes, thus dividing finely the hydrogel into particles about 1 to about 5 mm. Thereafter, the hydrogel was neutralized with 88.2 parts by weight of sodium carbonate.

The hydrogel was uniformly neutralized when the color of phenolphthalein, as used as the indicator, had entirely disappeared. Furthermore, the neutralized hydrogel was dried with a hot air dryer of 160° C. for 1 hour, and then pulverized with a portable pulverizer, and then classified with a sieve, thus obtaining water-absorbent resin (h) of which 97 wt % comprised particles with a particle diameter range of from 106 μm to less than 500 μm. The neutralization ratio of this water-absorbent resin was 75 mol %.

EXAMPLE 4

A surface-crosslinking agent comprising 0.1 parts by weight of propylene glycol, 0.03 parts by weight of glycerol polyglycidyl ether, 3 parts by weight of water, and 1 part by weight of isopropyl alcohol was mixed with 100 parts by weight of water-absorbent resin (f) as obtained in Referential Example 5. The resultant mixture was heated at 195° C. for 50 minutes, thus obtaining water-absorbing agent (4) according to the present invention. As to water-absorbing agent (4), Table 1 shows results of: the absorption capacity;

the absorption capacity under an increased pressure; the absorption capacity of the upper swollen gel layer under the increased pressure; the absorption capacity of the lower swollen gel layer under the increased pressure; the absorption efficiency under the increased pressure; and the kewpie doll test.

EXAMPLE 5

A surface-crosslinking agent comprising 1.0 part by weight of propylene glycol, 0.03 parts by weight of ethylene glycol diglycidyl ether, 3 parts by weight of water, and 1 part by weight of isopropyl alcohol was mixed with 100 parts by weight of water-absorbent resin (f) as obtained in Referential Example 5. The resultant mixture was heated at 185° C. for 35 minutes, thus obtaining water-absorbing agent (5) according to the present invention. As to water-absorbing agent (5), Table 1 shows results of: the absorption capacity; the absorption capacity under an increased pressure; the absorption capacity of the upper swollen gel layer under the increased pressure; the absorption capacity of the lower swollen gel layer under the increased pressure; the absorption efficiency under the increased pressure; and the kewpie doll test.

EXAMPLE 6

A surface-crosslinking agent comprising 1.0 part by weight of propylene glycol, 0.05 parts by weight of ethylene glycol diglycidyl ether, 3 parts by weight of water, and 3 parts by weight of isopropyl alcohol was mixed with 100 parts by weight of water-absorbent resin (g) as obtained in Referential Example 6. The resultant mixture was heated at 190° C. for 50 minutes, thus obtaining water-absorbing agent (6) according to the present invention. As to water-absorbing agent (6), Table 1 shows results of: the absorption capacity; the absorption capacity under an increased pressure; the absorption capacity of the upper swollen gel layer under the increased pressure; the absorption capacity of the lower swollen gel layer under the increased pressure; the absorption efficiency under the increased pressure; and the kewpie doll, test.

EXAMPLE 7

A surface-crosslinking agent comprising 1.0 part by weight of ethylene carbonate, 0.03 parts by weight of ethylene glycol diglycidyl ether, 3 parts by weight of water, and 1 part by weight of isopropyl alcohol was mixed with 100 parts by weight of water-absorbent resin (h) as obtained in Referential Example 7. The resultant mixture was heated at 190° C. for 50 minutes, thus obtaining water-absorbing agent (7) according to the present invention. As to water-absorbing agent (7), Table 1 shows results of: the absorption capacity; the absorption capacity under an increased pressure; the absorption capacity of the upper swollen gel layer under the increased pressure; the absorption capacity of the lower swollen gel layer under the increased pressure; the absorption efficiency under the increased pressure; and the kewpie doll test.

Comparative Example 3

A surface-crosslinking agent comprising 0.5 parts by weight of glycerol, 2 parts by weight of water, and 2 parts by weight of isopropyl alcohol was mixed with 100 parts by weight of water-absorbent resin (f) as obtained in Referential Example 5. The resultant mixture was heated at 190° C. for 50 minutes, thus obtaining comparative water-absorbing agent (3) not according to the present invention. As to comparative water-absorbing agent (3), Table 1 shows results of: the absorption capacity; the absorption capacity under an increased pressure; the absorption capacity of the upper swollen gel layer under the increased pressure; the absorption capacity of the lower swollen gel layer under the increased pressure; the absorption efficiency under the increased pressure; and the kewpie doll test.

Comparative Example 4

A surface-crosslinking agent comprising 0.5 parts by weight of glycerol, 0.05 parts by weight of glycerol polyglycidyl ether, 3 parts by weight of water, and 1 part by weight of isopropyl alcohol was mixed with 100 parts by weight of water-absorbent resin (h) as obtained in Referential Example 7. The resultant mixture was heated at 180° C. for 20 minutes, thus obtaining comparative water-absorbing agent (4) not according to the present invention. As to comparative water-absorbing agent (4), Table 1 shows results of: the absorption capacity; the absorption capacity under an increased pressure; the absorption capacity of the upper swollen gel layer under the increased pressure; the absorption capacity of the lower swollen gel layer under the increased pressure; the absorption efficiency under the increased pressure; and the kewpie doll test.

TABLE 1

|  |  | Amount of eluting component in water-absorbent resin used (wt %) | Absorption capacity (g/g) | Absorption capacity under increased pressure (g/g) | Absorption capacity of upper swollen gel layer under increased pressure (g/g) | Absorption capacity of lower swollen gel layer under pressure increased (g/g) | Absorption efficiency under increased pressure | Number of times of injection into each kewpie doll | | |
| --- | --- | --- | --- | --- | --- | --- | --- | --- | --- | --- |
|  |  |  |  |  |  |  |  | Doll 1 | Doll 2 | Doll 3 |
| Example 1 | Water-absorbing agent (1) | 0.5 | 28.4 | 34.6 | 27.9 | 36.1 | 0.77 | 4 | 4 | 3 |
| Example 2 | Water-absorbing agent (2) | 0.1 | 31.1 | 34.8 | 28.6 | 37.8 | 0.76 | 4 | 3 | 4 |
| Example 3 | Water-absorbing agent (3) | 0.1 | 37.1 | 39.6 | 31.7 | 43.7 | 0.73 | 4 | 4 | 4 |
| Example 4 | Water-absorbing agent (4) | — | 35.2 | 36.5 | 26.8 | 41.3 | 0.65 | 4 | 4 | 3 |

TABLE 1-continued

|  |  | Amount of eluting component in water-absorbent resin used (wt %) | Absorption capacity (g/g) | Absorption capacity under increased pressure (g/g) | Absorption capacity of upper swollen gel layer under increased pressure (g/g) | Absorption capacity of lower swollen gel layer under increased pressure (g/g) | Absorption efficiency under increased pressure | Number of times of injection into each kewpie doll |  |  |
|---|---|---|---|---|---|---|---|---|---|---|
|  |  |  |  |  |  |  |  | Doll 1 | Doll 2 | Doll 3 |
| Example 5 | Water-absorbing agent (5) | — | 37.6 | 38.0 | 28.6 | 43.7 | 0.65 | 4 | 4 | 4 |
| Example 6 | Water-absorbing agent (6) | — | 38.6 | 40.5 | 31.4 | 46.0 | 0.68 | 4 | 4 | 4 |
| Example 7 | Water-absorbing agent (7) | — | 39.2 | 35.3 | 22.0 | 46.0 | 0.48 | 4 | 3 | 4 |
| Comparative Example 1 | Comparative water-absorbing agent (1) | 5.5 | 33.0 | 34.4 | 23.7 | 40.1 | 0.59 | 3 | 3 | 3 |
| Comparative Example 2 | Comparative water-absorbing agent (2) | 5.5 | 28.9 | 32.1 | 23.3 | 36.4 | 0.64 | 3 | 3 | 3 |
| Comparative Example 3 | Comparative water-absorbing agent (3) | — | 38.2 | 29.8 | 15.5 | 43.2 | 0.36 | 3 | 3 | 3 |
| Comparative Example 4 | Comparative water-absorbing agent (4) | — | 39.6 | 31.6 | 15.8 | 45.0 | 0.35 | 3 | 3 | 3 |

As is clear from the results as shown in Table 1, the water-absorbing agent according to the present invention displays high absorption efficiency under an increased pressure. Such a water-absorbing agent was obtained for the first time by a process in which, like in Examples 1 to 3, a water-absorbent resin, having an amount of the eluting component of 1 part by weight or less per 100 parts by weight of the water-absorbent resin, was heated in the presence of a surface-crosslinking agent, or by a process in which: like in Examples 4 to 7, the particle diameter of a water-absorbent resin was adjusted so as to substantially fall within the range of from 106 to less than 500 μm by operations such as classification; and the resin was then heated in the presence of two or more surface-crosslinking agents of different solubility parameter ranges.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A polymeric or copolymeric water-absorbing agent, comprising, in combination:
    a) an absorption capacity of 30 g/g or more under an increased pressure which is greater than atmospheric pressure;
    b) an absorption efficiency of 0.7 or more under the increased pressure, wherein the absorption efficiency under the increased pressure is determined by the following method:
        i) disposing the water-absorbing agent in a receptacle;
        ii) permitting the water-absorbing agent to absorb a fluid while bringing a downwardly vertical pressure of 50 g/cm$^2$ to bear on the water-absorbing agent for 60 minutes; then
        iii) after absorption, dividing the resultant gel into three equal gel layers by weight, with the three equal gel layers being an upper gel layer, a middle gel layer, and a lower gel layer; then
        iv) determining the absorption capacity of the upper gel layer and determining the absorption capacity of the lower gel layer; then
        v) determining absorption efficiency by dividing the absorption capacity of the upper gel layer by the absorption capacity of the lower gel layer.

2. A polymeric or copolymeric water-absorbing agent, comprising, in combination:
    a) an absorption capacity of a lower swollen gel layer of 45 g/g or more under an increased pressure which is greater than atmospheric pressure;
    b) an absorption efficiency of 0.4 or more under the increased pressure, wherein the absorption efficiency under the increased pressure is determined by the following method:
        i) disposing the water-absorbing agent in a receptacle;
        ii) permitting the water-absorbing agent to absorb a fluid while bringing a downwardly vertical pressure of 50 g/cm$^2$ to bear on the water-absorbing agent for 60 minutes; then
        iii) after absorption, dividing the resultant gel into three equal gel layers by weight, with the three equal gel layers being an upper gel layer, a middle gel layer, and a lower gel layer; then
        iv) determining the absorption capacity of the upper gel layer and determining the absorption capacity of the lower gel layer; then
        v) determining absorption efficiency by dividing the absorption capacity of the upper gel layer by the absorption capacity of the lower gel layer.

3. A polymeric or copolymeric water-absorbing agent, comprising, in combination:
    a) an absorption capacity of a lower swollen gel layer of 30 g/g or more under an increased pressure which is greater than atmospheric pressure;
    b) an absorption efficiency of 0.3 or more under the increased pressure, wherein the absorption efficiency under the increased pressure is determined by the following method:
        i) disposing the water-absorbing agent in a receptacle;
        ii) permitting the water-absorbing agent to absorb a fluid while bringing a downwardly vertical pressure of 50 g/cm$^2$ to bear on the water-absorbing agent for 60 minutes; then
        iii) after absorption, dividing the resultant gel into three equal gel layers by weight, with the three equal gel layers being an upper gel layer, a middle gel layer, and a lower gel layer; then iv) determining the absorption capacity of the upper gel layer and determining the absorption capacity of the lower gel layer; then v) determining absorption efficiency by dividing the absorption capacity of the upper gel layer by the absorption capacity of the lower gel layer; and c) with a relationship between the absorption efficiency under the increased pressure and the absorption capacity of the lower swollen gel layer under the increased pressure being defined by the following equation: absorption efficiency under increased pressure<1.82−2.93×10$^{-2}$ ×(absorption capacity of the lower swollen gel layer under increased pressure).

4. The water-absorbing agent according to claim 1, in combination with a fibrous material to form an absorbent material.

5. The water-absorbing agent according to claim 2, in combination with a fibrous material to form an absorbent material.

6. The water-absorbing agent according to claim 3, in combination with a fibrous material to form an absorbent material.

7. The water-absorbing agent according to claim 4, in combination with a liquid-permeable sheet, a liquid-impermeable sheet and an absorbent layer interposed between the sheets, wherein the absorbent layer comprises the absorbent material.

8. The water-absorbing agent according to claim 5, in combination with a liquid-permeable sheet, a liquid-impermeable sheet and an absorbent layer interposed between the sheets, wherein the absorbent layer comprises the absorbent material.

9. The water-absorbing agent according to claim 6, in combination with a liquid-permeable sheet, a liquid-impermeable sheet and an absorbent layer interposed between the sheets, wherein the absorbent layer comprises the absorbent material.

10. The water-absorbing agent according to claim 1, wherein the water-absorbing agent is produced by a process comprising the following step:

a) heating, in the presence of a surface-crosslinking agent, a water-absorbent resin having an absorption capacity of 40 (g/g) or more and an amount of an eluting component of 1 part by weight or less per 100 parts by weight of the water-absorbent resin.

11. The water-absorbing agent according to claim 10, wherein the water-absorbent resin is treated with a hydrophilic solution prior to said step of heating.

12. The water-absorbing agent according to claim 1, wherein the water absorbing agent is produced by a process comprising the following steps:

a) polymerizing a water-absorbent resin in the presence of a water-soluble chain transfer agent;

b) treating the polymerized water-absorbent resin with a hydrophilic solution; and c) heating the treated water-absorbent resin in the presence of a surface-crosslinking agent to obtain the water-absorbing agent.

13. The water-absorbing agent according to claim 1, wherein the water absorbing agent is produced by a process comprising the following steps:

a) treating with a hydrophilic solution a water-absorbent resin of which the weight-average molecular weight of an eluting component is 200,000 or less; and b) heating the treated water-absorbent resin in the presence of a surface-crosslinking agent to obtain the water absorbing agent.

14. The water-absorbing agent according to claim 10, wherein the step of heating is carried out at a temperature in the range of 160° C. to 200° C.

15. The water-absorbing agent according to claim 1, wherein the water-absorbing agent comprises a surface crosslinked water-absorbent resin which, prior to being surface-crosslinked, comprised a low eluting water-absorbent resin having an absorption capacity of 40 (g/g) or more and an amount of an eluting component of 1 part by weight or less per 100 parts by weight of said low eluting water-absorbent resin.

16. A polymeric or copolymeric water-absorbing agent in combination with a test for determining an efficiency of absorption of the polymeric or copolymeric water-absorbing agent, wherein the test for determining efficiency of absorption comprises the steps of:

a) disposing the water-absorbing agent in a receptacle;

b) permitting the water-adsorbing agent to absorb a fluid while bringing a downwardly generally vertical pressure to bear on the water-absorbing agent for a predefined period of time;

c) dividing a resultant gel into predefined layers, with at least one of the layers being an uppermost layer and with at least one of the other layers being a lowermost layer;

d) determining an absorption capacity of each of the uppermost and lowermost layers; and then e) determining the efficiency of absorption by relating the absorption capacity of the uppermost layer to the lowermost layer.

* * * * *